May 23, 1972 L. H. SHOESMITH Plant Pat. 3,192

CHRYSANTHEMUM PLANT (POLAR BEAUTY)

Filed Oct. 5, 1970

INVENTOR.
LEONARD H. SHOESMITH

BY Rummler & Snow
ATTYS

United States Patent Office

Plant Pat. 3,192
Patented May 23, 1972

3,192

CHRYSANTHEMUM PLANT (POLAR BEAUTY)

Leonard H. Shoesmith, Westfield-Woking, Surrey, England, assignor to Pan-American Plant Company, West Chicago, Ill.

Filed Oct. 5, 1970, Ser. No. 78,311
Int. Cl. A01h *5/00*
U.S. Cl. Plt.—77 1 Claim

ABSTRACT OF THE DISCLOSURE

A new variety of chrysanthemum plant of the standard semi-incurved type producing very large white blossoms, when disbudded, and being suitable for year-around flowering with a ten week response period. The plant has a vigorous and strong upright growth habit and the blossom is durable and long lasting with a large amount of petalage which appears cream color as it opens, later turning to pure white.

BACKGROUND OF THE NEW PLANT

This white crysanthemum plant was discovered by me during extensive breeding activity carried on by me since 1967 at West Chicago, Ill., with the object of developing improved chrysanthemum plants of distinctive form and color and commercially advantageous growth habits for greenhouse production of cut flowers. This new variety of chrysanthemum originated as a seedling product of random crossing of various standard greenhouse plants and was selected from many thousands of them, for propagation and test, because of the clean white color of its blooms and its apparent habit of vigorous and erect growth. Asexual propagation by vegetative cuttings, carried on by me at West Chicago, Ill., has showed the new plant to produce a good, long lasting flower of very large size on a strong erect stem, when disbudded, as well as a ten week response with photoperiod culture and a capability of being flowered at any time of the year, particularly during summer months. Extensive propagation, by means of vegetative cuttings, at West Chicago, Ill., and at Cortez, Fla., has demonstrated that the beforementioned features and advantages come true from generation to generation and are firmly fixed.

DESCRIPTION OF THE DRAWINGS

This new variety of white chrysanthemum plant is illustrated by the accompanying drawing in which the principal figure shows the form of the blossom in full color, as nearly true as it is reasonably possible to obtain by conventional photographic processes, and the ink drawn figures show the distinctive configuration of typical leaves of the new plant.

DESCRIPTION OF THE NEW PLANT

Figure 1:
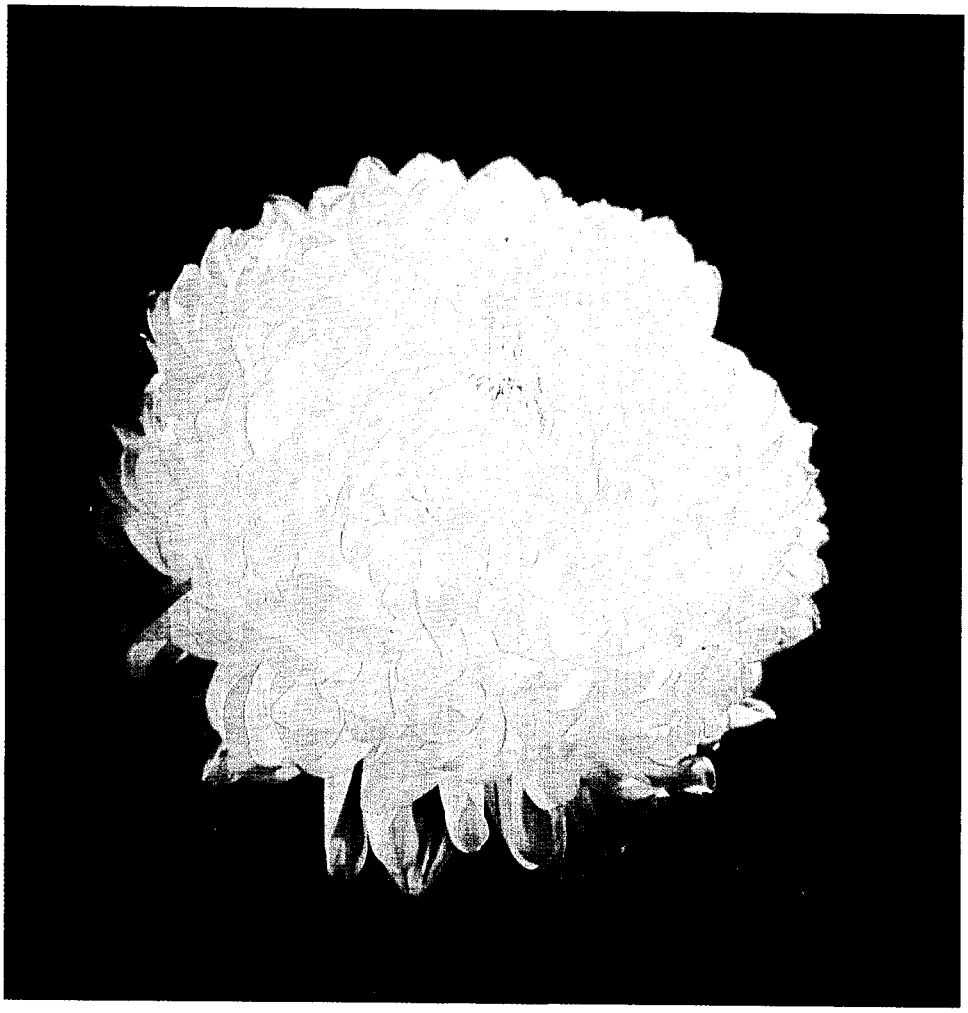
Figure 2:
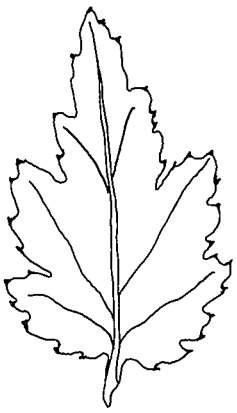
Figure 3:
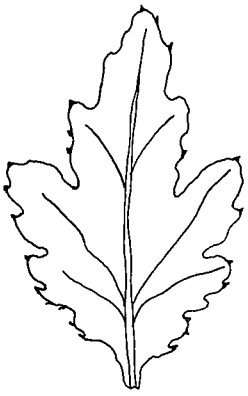

The following is a detailed description of my new chrysanthemum plant, any color designations by code being according to the Horticultural Colour Chart issued by the British Colour Council.

*The plant*

Origin: Seedling selected from many random crosses.
Parentage: Unknown.
Classification:
*Botanic.*—*Chrysanthemum morifolium.*
*Commercial.*—Standard semi-incurved.

Form: Naturally bush—grown as a single stem standard.
Height: Three feet.
Growth: Vigorous, strong, sturdy, upright and normally branching.
Foliage: Quantity: semi-abundant, with about 13 leaves on a 3 foot stem.
*Leaf size.*—Approximately 4 to 4½ inches long x about 2 inches wide.
*Shape.*—Pointed, serrated, lobed lanceolate.
*Texture.*—Smooth.
*Color.*—Upper side—Spinach Green 0960. Under side—Spinach Green 0960/3.
*Ribs and veins.*—Pinnate.
*Petioles.*—About 2 inches long.

*The bud*

Form: Round and flat topped—generally globular. Diameter: ¾ inch; depth: ⅜ inch.
Opening rate: Slowly—3 to 4 weeks.
Color:
*When sepals first divide.*—Cream shade of White.
*When petals begin to unfurl.*—Cream.
Sepals: Spear-shaped and stand up. Color:
*Inside.*—Scheeles Green 860.
*Outside.*—Scheeles Green 860.
Calyx:
*Shape.*—Round and flat.
*Aspect.*—Smooth.
Peduncle: Erect, slightly tomentose, 2 inches long. Color: Scheeles Green.

*The flower*

Blooming period: Natural season flowering in early November; photoperiod responsive for year-around flowering; 10 week response period.
Size: Very large. Diameter—6 inches; depth—3 inches.
Borne: Singly when disbudded. Naturally racemose.
Shape: When bloom first opens—Ovoid, with high center. Shape does not change with maturity.
Petalage: Petals are many in number and in composite arrangement.
*Form.*—Ray floret, rounded end with tendency to form a mucronate tip.
*Color.*—Outer petal—White. Inside petal—Cream. Reverse side—White.
*Texture.*—Soft. Appearance—Satiny.
Peduncle: Sturdy and upright, 3 to 4 inches long. Color: Green.
Persistence: Petals hang on and dry. Bloom is not affected by wet or hot weather and there is no discoloration after full bloom.
Lasting quality: Bloom is long lasting whether on plant or as a cut flower.

*Reproductive organs*

Stamens:
*Anthers.*—Numerous, in disc arrangement, each about ⅛ inch long.
*Filaments.*—¼ inch long and Yellow in color.
*Pollen.*—Yellow in color.
Pistils: One for each ray floret, ¼ inch long.
Stigmas: Yellow in color.
Characteristics of ovaries: Insignificant.

The principal distinctions of my new variety of chrysanthemum plant are to be found in the clean white semi-incurved flower with its large amount of petalage which appears cream colored as the blossom opens and then turns to pure white as the bloom reaches the fully opened state; in the durable long-lasting quality of the flower and the strong, sturdy, upright habit of growth; and in the uniform ten week response to photoperiod culture.

I claim:

1. The new and distinct variety of chrysanthemum plant of the standard semi-incurved type, substantially as herein shown and described, characterized by the clean white color of its very large, many petaled blooms, by its vigorous, strong and upright growth, and by its ability to be flowered the year-around with a consistent ten week response to photoperiod culture as a greenhouse plant.

No references cited.

ROBERT E. BAGWILL, Primary Examiner